(12) United States Patent
Felder et al.

(10) Patent No.: US 11,837,068 B2
(45) Date of Patent: Dec. 5, 2023

(54) COMPUTER IMPLEMENTED SYSTEM AND METHOD FOR CORRECT NECK POSTURE

(71) Applicants: Saaya Felder, Wesley Chapel, FL (US); Rajyn Jarrod Felder, Wesley Chapel, FL (US); Fred J. Felder, Wesley Chapel, FL (US); Nisha K. Sharma-Felder, Wesley Chapel, FL (US)

(72) Inventors: Saaya Felder, Wesley Chapel, FL (US); Rajyn Jarrod Felder, Wesley Chapel, FL (US); Fred J. Felder, Wesley Chapel, FL (US); Nisha K. Sharma-Felder, Wesley Chapel, FL (US)

( * ) Notice: Subject to any disclaimer, the term of this patent is extended or adjusted under 35 U.S.C. 154(b) by 0 days.

(21) Appl. No.: 17/727,902

(22) Filed: Apr. 25, 2022

(65) Prior Publication Data

US 2022/0343745 A1 Oct. 27, 2022

Related U.S. Application Data

(60) Provisional application No. 63/180,198, filed on Apr. 27, 2021.

(51) Int. Cl.
*G08B 21/04* (2006.01)

(52) U.S. Cl.
CPC ................. *G08B 21/0446* (2013.01)

(58) Field of Classification Search
None
See application file for complete search history.

(56) References Cited

U.S. PATENT DOCUMENTS

| | | | | |
|---|---|---|---|---|
| 2012/0026322 | A1* | 2/2012 | Malka | G01C 11/02 348/135 |
| 2014/0176333 | A1* | 6/2014 | Tsuji | G06F 1/1624 340/689 |
| 2018/0197395 | A1* | 7/2018 | Kuwana | G06F 3/017 |
| 2019/0213402 | A1* | 7/2019 | Yang | G06V 40/20 |
| 2019/0287304 | A1* | 9/2019 | Davies | G06T 7/73 |
| 2021/0304581 | A1* | 9/2021 | Franklin | G08B 21/06 |

* cited by examiner

*Primary Examiner* — John F Mortell
(74) *Attorney, Agent, or Firm* — Brennan, Manna & Diamond, LLC

(57) ABSTRACT

The present invention relates to a computer-implemented system and method for preventing users from bending their necks too far forward or past thirty degrees away from vertical during viewing of a handheld electronic device. The system uses a computer-implemented application installed in the device that determines flexion of the user's neck and compares with a threshold to determine a 'tech neck' condition. The application generates an alert displayed on the screen of the device to indicate the 'tech neck' condition and further, can pause or hang the display when the 'tech neck' condition is continued to be determined. The system and method assist in preventing injuries, strains and disabilities to both children and adults that use electronic devices for extended periods of time.

20 Claims, 7 Drawing Sheets

COMPUTER IMPLEMENTED SYSTEM AND METHOD FOR CORRECT NECK POSTURE

CROSS-REFERENCE TO RELATED APPLICATION

The present application claims priority to, and the benefit of, U.S. Provisional Application No. 63/180,198, which was filed on Apr. 27, 2021 and is incorporated herein by reference in its entirety.

FIELD OF THE INVENTION

The present invention relates generally to the field of neck posture correction systems and methods. More specifically, the present invention relates to a 'tech neck' prevention software application and system designed to prevent users from suffering from 'tech neck' syndrome; a term used to describe flexion of the neck when looking at an electronic device. The system generates an alert on the electronic device to alert the user of incorrect position or posture of the neck. The system can also pause the operation of the device which is then resumed once the neck of the user viewing the device is in an optimal position. Accordingly, the present disclosure makes specific reference thereto. Nonetheless, it is to be appreciated that aspects of the present invention are also equally applicable to other like applications, devices and methods of manufacture.

BACKGROUND

By way of background, use of smartphones and other handheld electronic devices has been growing at a rapid pace. Specifically, smartphones have become a part of people's lives and individuals spend a lot of time on their electronic devices. Medical studies have suggested that individuals spend around 1,400 hours per year bending their neck forward while using their smartphones and other handheld electronic devices. The time can be up to 3,000 hours per year for young individuals such as teenagers. From this growing usage of electronic devices and especially smartphones, concerns have arisen from a healthcare perspective. Individuals often suffer back and neck pain due to extended use of electronic devices, such as a tablet, a smartphone, a laptop, and/or other such types of devices. Such pain may be called 'tech neck', an overuse syndrome or a repetitive stress/strain injury to the neck caused by holding the head/neck forward and in a downward position for extended periods of time in order to view a hand-held electronic device such as a smart cellphone. 'Tech neck' results in acute and chronic pain and may require long term treatment.

In use, smart Cellphones and PDAs can be used for hours with the neck of a user in a forward bent position known medically as cervical flexion. Cervical flexion is the bending or canting of the head forward towards the chest. As the head of the user is in bent position for hours, more pressure is applied to a small disk between the spine and vertebra. Also, using electronic devices such as a laptop or smartphone involves looking down and away which may lead to poor posture and may create or exacerbate cervical flexion, pain and/or injury. The aforementioned 'tech neck' postures can cause various problems including pain and these problems are commonly referred to as 'tech neck' syndrome. If these symptoms are exacerbated, disks in the neck can be aggravated.

The 'tech neck' syndrome can occur if the user unconsciously and habitually maintains bad posture for a long period of time. Thus, it is important for the user not to take a bad posture position for a long period of time which can cause 'tech neck' syndrome. There is a need for a measure to prevent the 'tech neck' and continuous forward bending of neck and face of the user using the electronic device. Further, the prevention should be real-time and convenient for the user.

Therefore, there exists a long felt need in the art for a system that prevents users from suffering from 'tech neck' syndrome when looking at their electronic devices such as smartphones. There is also a long felt need in the art for a system that prevents users from bending their necks too far forward during use of the electronic device. Additionally, there is a long felt need in the art for the 'tech neck' prevention system that alerts the users using the electronic device to reposition their neck posture. Moreover, there is a long felt need in the art for a 'tech neck' software application for the electronic devices that can instruct the user to move their neck and let them know when optimal positioning has been reached. Finally, there is a long felt need in the art for the software based 'tech neck' prevention method that prevents users such as children or adults from injuries and disabilities that can occur because of the use of electronic devices for long hours.

The subject matter disclosed and claimed herein, in one embodiment thereof, comprises a software-based 'tech neck' prevention method that prevents the user from 'tech neck' syndrome while looking at the electronic device. The 'tech neck' software application can be downloaded in various types of electronic devices such as laptops, tablets, smartphones or other such types of electronic devices. The software application prevents users from bending or canting their necks too far forward, for example past thirty degrees from vertical, while viewing the electronic devices. The software application detects when the user's neck is in flexion past a predeterminable angle, i.e. thirty degrees from vertical, and displays a visual alert in the corner of the screen to reposition the neck. The software application can pause the use of the device until the user moves the neck into a healthy or more vertical position for viewing. The application instructs the user to move the neck and restart the device when optimal or preferred positioning is reached.

In this manner, the computer implemented 'tech neck' prevention system and application of the present invention accomplishes all of the forgoing objectives, and provides a relatively safe, easy and convenient solution to prevent users from being afflicted with 'tech neck' syndrome while looking at an electronic device. The system and application detects the flexion of a user's neck and displays a visual alert in the corner of the screen to reposition the neck. Additionally, the system and application instructs the user to move the neck and indicates to the user when optimal positioning of the neck has been reached.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a computer-implemented method for preventing users from bending or canting their necks too far forward, for example past thirty degrees, during viewing of a smartphone. The method includes the steps of receiving, by a computer-implemented software application installed in the smartphone, flexion or canted angle of the neck of the user; receiving by the application, the face image of the user; receiving by the application, tilt angle of the smartphone using gyroscope and accelerometer of the smartphone; determining an accurate flexion or cant angle of the neck by calibrating the received flexion with the tilt angle, wherein the flexion is also based on face image of a user; comparing, by the application, the determined flexion with a threshold value to determine a 'tech neck' condition; and, displaying, by the application, upon determining the 'tech neck' condition, a visual notification on the top right corner of the display of the smartphone indicating to the user to correct the neck position.

In yet another embodiment, the method further includes the step of decreasing brightness of the display of the smartphone when the 'tech neck' condition is continued to be determined by the application.

In yet another embodiment, the determination of the 'tech neck' is performed locally in the smartphone using the processor of the smartphone.

In yet another embodiment, the determination of the 'tech neck' is performed in a cloud server.

In yet another embodiment, the predeterminable or threshold value is thirty degrees of flexion of the neck measured from a vertical reference.

The subject matter disclosed and claimed herein, in another embodiment thereof, comprises a computer-implemented application for preventing handheld electronic device users from bending their necks too far forward, for example past thirty degrees, during use of the device. The application causes the processor of the device to determine bending or canting angle of the neck of the user to determine flexion, generating a visual or audio alert when the bending angle is determined to be more than thirty degrees, pausing or hanging the display of the device when the bending or canting angle is continued to be more than thirty degrees and restarting or resuming the device when the neck has a forward bend of less than thirty degrees.

In yet another embodiment, the electronic device can be one or more of a smartphone, a tablet, a PDA, a smartwatch or a laptop.

In yet another embodiment, a 'tech neck' prevention system is disclosed. The system includes a handheld electronic device having a computer-implemented software application. The application has a plurality of software modules, a face detection module for detecting the face and eyes of a user viewing the device, a neck position module for detecting neck flexion, a flexion calculation module for determining neck flexion using device tilt detected by the electronic device tilt module and a comparison module for comparing the determined tilt with a threshold or predeterminable value.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
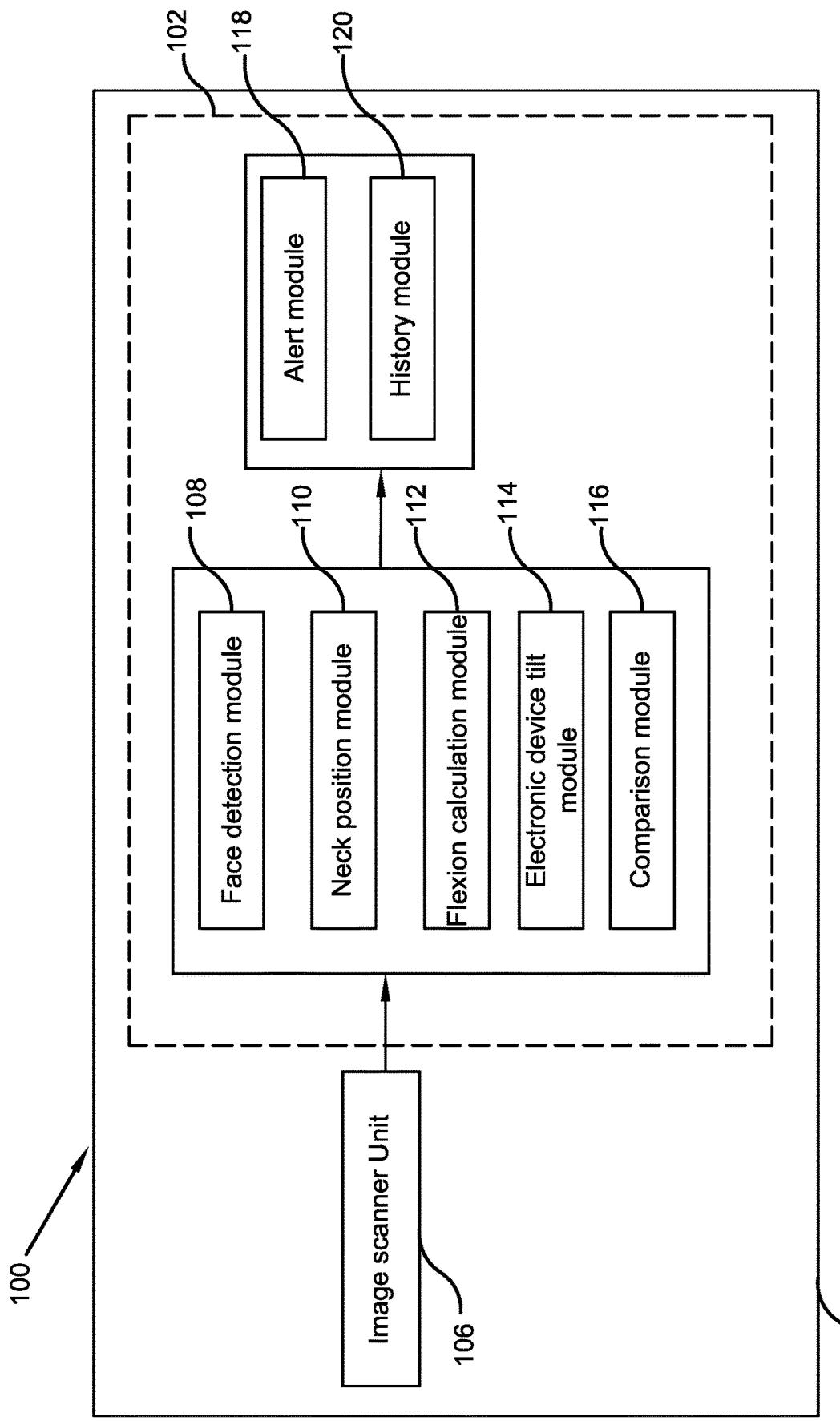
FIG. 1 illustrates a block diagram view of a computer-implemented 'tech neck' prevention system of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for a system that prevents users from suffering from 'tech neck' syndrome when looking at their electronic devices such as smartphones. There is also a long felt need in the art for a system that prevents users from bending their necks too far forward during use of the electronic device. Additionally, there is a long felt need in the art for the 'tech neck' prevention system that alerts the users using the electronic device to reposition their neck posture. Moreover, there is a long felt need in the art for a 'tech neck' software application for the electronic devices that instructs users to move their necks and lets them know when optimal positioning has been reached. Finally, there is a long felt need in the art for the software-based 'tech neck' prevention method that prevents users, such as children or adults, from injuries and disabilities that can occur because of the use of electronic devices for long periods of time.

The present invention, in one exemplary embodiment, is a computer-implemented method for preventing users from bending their necks too far forward, i.e. past thirty degrees, during viewing or use of a smartphone. The method includes the steps of receiving, by a computer-implemented software application installed in the smartphone, flexion of neck of the user; receiving by the application, a face image of the user; receiving by the application, tilt angle of the smartphone using gyroscope and accelerometer of the smartphone; determining an accurate flexion of the neck by calibrating the received flexion with the tilt angle wherein the flexion is also based on face image of a user; comparing, by the application, the determined flexion with a threshold value to determine a 'tech neck' condition; and, displaying, by the application, on determining the 'tech neck' condition, a visual notification on the top right corner of the display of the smartphone indicating to correct neck position of the user.

Referring initially to the drawings, FIG. 1 illustrates a block diagram view of computer-implemented 'tech neck' prevention system of the present invention in accordance with the disclosed architecture. The computer-implemented 'tech neck' prevention system 100 is designed based on a 'tech neck' prevention software application 102 that is configured to be installed in electronic devices 104 such as mobile cellphones, laptops, tablets, smartwatches, or more. It should be noted that the computer-implemented instructions of the software application 102 can be encoded in operating systems of such an electronic device 104. The 'tech neck' prevention system 100 is designed to analyze a user's neck posture or canted angle when the user is using the electronic device 104. More specifically, the 'tech neck' software application 102 provides feedback and instruction to the user of the electronic device 104 to maintain a healthy posture while using the device 104 and thus helps in protecting the user from 'tech neck' syndrome such as cervical kyphosis, or other such type of injuries, disabilities, muscle strains, and/or discomforts caused due to incorrect posture while using the device 104. It should be noted that the 'tech neck' software application 102 can operate in the background while the user works or views any other application on the device 104. The software application 102 is configured to monitor the neck posture of the user during use of the device 104 and provides instructions and notifications to the user.

It is to be appreciated that the 'tech neck' software application 102 of the present invention provides a visual and/or audible alert notification to the user whenever the user uses the electronic display device 104 in an incorrect viewing position/posture. The 'tech neck' software application 102 is configured to protect the user from the frequent painful condition that results when the user bends or cants the neck too far forward or past 30 degrees from vertical while using/viewing the electronic device 104.

In operation, the 'tech neck' software application 102 continuously scans an image or records video of the user's face when the user is using the device 104. The scanning/recording is performed through an image scanner unit 106 of the electronic device 104. The scanner unit 106 can be a camera disposed on the front of the device 104 that is generally used as a selfie camera. The application 102 is provided permission to access the digital camera 106 of the electronic device 104.

The software application 102 has encoded computer readable instructions that are logically stored in the form of modules. The modules are configured to perform various functions that are configured to display instructions on the display of the electronic device 104. A face detection module 108 detects the face and position of the face when a user is using the electronic device 104. The face detection module 108 creates a 3D map of the face and detects the position of the eyes of the user. When the eyes are detected to be looking at the screen/display of the electronic device 104, the face position of the user is detected. In parallel to the face detection module 108, a neck position module 110 detects and calculates a position of the neck of the user using the device 104. The neck position module 110 is specifically configured to detect and calculate the neck flexion area disposed under the face area. The flexion calculation module 112 is configured to use the measurements and position of the face and the canted neck detected by the face detection module 108 and neck position module 110 and construct a virtual 3D triangle to calculate the flexion or canted angle.

A user keeps the device 104 at various angles while using the electronic device 104, therefore, the electronic device tilt module 114 of the software application 102 detects the tilt or slope of the electronic device 104. The Electronic device's gyroscope and accelerometer are used by the tilt module 114 for determining tilt of the device 104. The flexion value determined by the flexion calculation module 112 and the tilt of the device 104 determined by the tilt module 114 are used for determining the 'tech neck' problem of the user. The comparison module 116 determines whether the user has bent or canted the neck too far forward or past 30 degrees from vertical during viewing by comparing the flexion determined by the flexion module 112 (calibrated with the tilt of the electronic device 104) with a predetermined threshold angle, thirty degrees for example. The predetermined threshold angle can be adjusted in the software application 102 as per the preferences of the user.

The 'tech neck' software application 102 includes a feedback alert module 118 configured to provide a visual and/or audio alert to the user to instruct a repositioning of the neck to an optimal position. The alert module 118 generates an alert when the comparison module 116 determines that the user's neck is in flexion past thirty degrees. The alert module 118 may also pause the use of the device 104, by freezing the display or making the device 104 unresponsive until the user moves the neck into a healthy position for viewing, typically less than thirty degrees. An alert can be in the form of a visual notification on the display and may also include a vibration or a beep sound to alert the user. Further, the vibration or the beep sound may stop when the user moves the electronic display device to the correct or preferred viewing angle.

The 'tech neck' software application 102 also includes a history module 120 that records the flexion information of the user using the electronic device 104. The alert module 118 can also include the additional information retrieved from the history module 120 in the notification. An example of such information is the number of times the flexion is detected more than thirty degrees. It should be noted that the software application 102 is programmed to have instructions for detecting whether the user's neck flexion is too far forward or past thirty degrees from vertical during use of the device 104 and instructs the user to move the neck to an optimal or preferred position for safe and convenient use of the electronic device 104.

It should be appreciated that, the electronic device 104 stated above in the disclosure in accordance with embodiments of the present invention can include a dedicated or discrete portable device having a display, suitable sensors, and a suitable processor or controller programmed with instructions to carry out various processes according to embodiments of the present technology.

Figure 2:
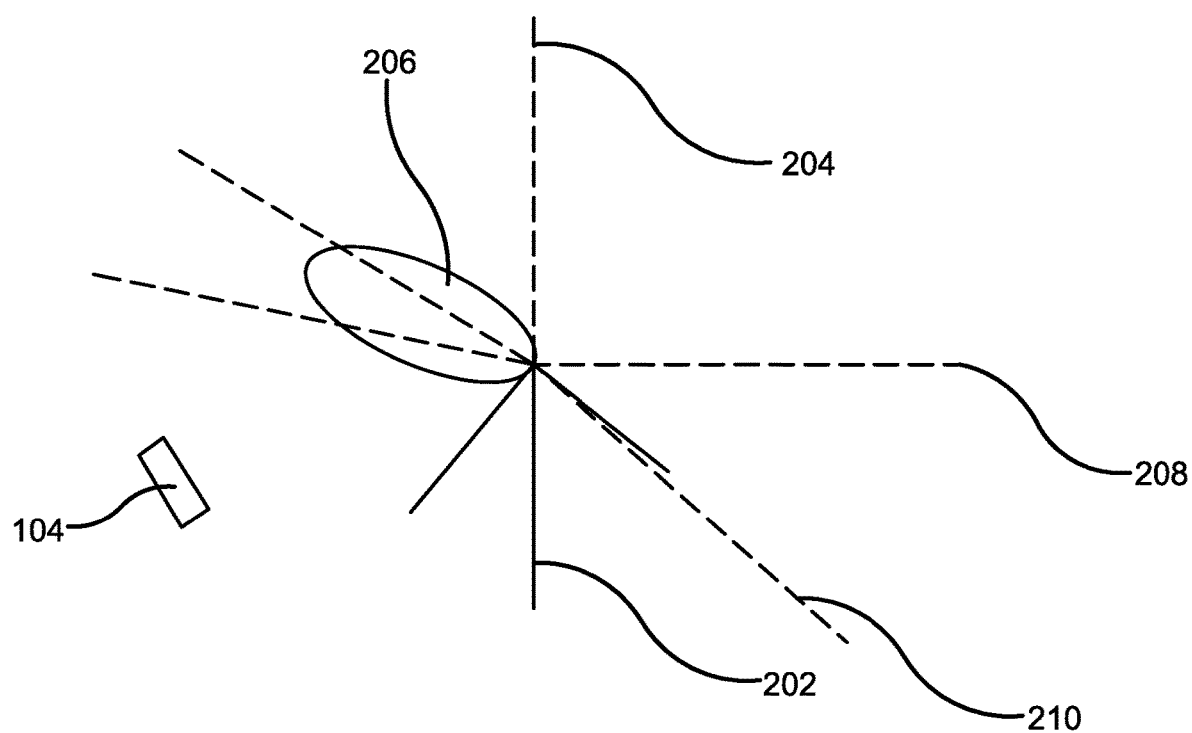
FIG. 2 illustrates a perspective view showing how the software application determines the flexion of the neck of a user while the user uses the smartphone or electronic device in accordance with the disclosed architecture.

FIG. 2 illustrates a perspective view showing how the software application 102 determines the flexion of the neck of a user while the user uses the smartphone or electronic device in accordance with the disclosed architecture. As shown, the user 202 is using the smartphone/electronic device 104 wherein the 'tech neck' software application 102 is installed on the device 104. The electronic device tilt module 114 uses the gyroscope and accelerometer of the electronic device 104 to calculate the tilt of the smartphone/device 104 relative to the imaginary vertical axis 204 using the imaginary smartphone tilt slope 210. Simultaneously, the neck position module 110 calculates the flexion of the neck 206 between the imaginary cervical axis 208 and the imaginary vertical axis 204. The smartphone tilt and the neck flexion of the user 202 is used by the smartphone application 102 for providing feedback alert to the user 202 for maintaining an optimal posture by the user 202. When the flexion of the neck is detected past thirty degrees, the feedback alert is generated by the application 102.

Figure 3:
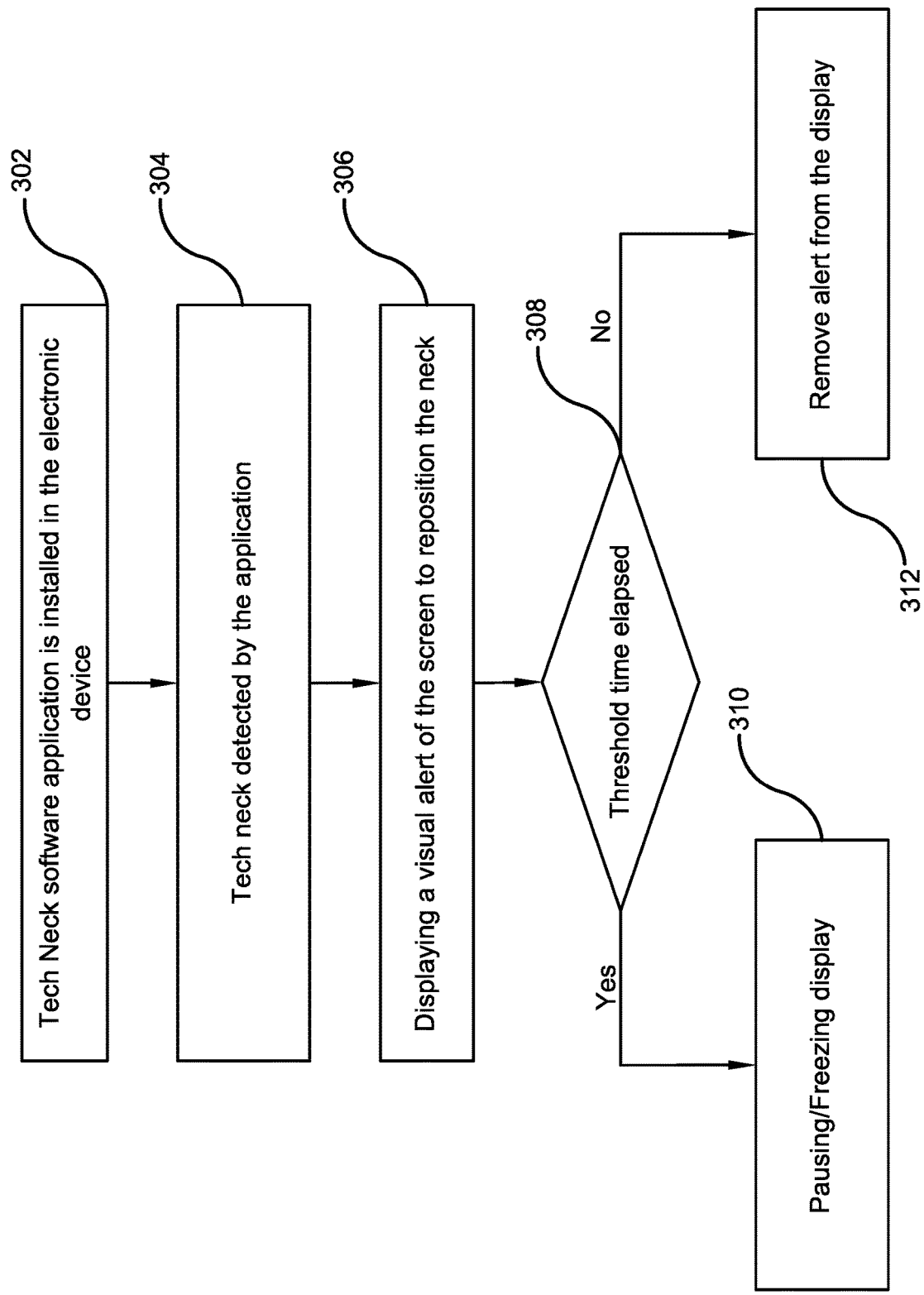
FIG. 3 illustrates a flow diagram showing exemplary steps performed in operation of the 'tech neck' software application for preventing a user from 'tech neck' syndrome in accordance with the disclosed architecture.

FIG. 3 illustrates a flow diagram showing exemplary steps performed in operation of the 'tech neck' software application 102 for preventing a user from 'tech neck' syndrome in accordance with the disclosed architecture. Initially a user installs the 'tech neck' software application in an electronic device such as a mobile device, laptop, tablet and/or other such type of handheld electronic device (Block 302). Then, the 'tech neck' software application detects whether the user neck flexion exceeds thirty degrees in a manner described in FIG. 2 (Block 304). Upon detecting the 'tech neck' condition of the user, the 'tech neck' software application installed on the electronic device provides a visual alert on the display of the electronic device, preferably at the corner of the display wherein the alert indicates the user to reposition the neck to an optimal or preferred position (Block 306). Then, the software application determines a time period for which the alert is displayed on the display (Block 308). In cases where a threshold time period has elapsed and the 'tech neck' is still detected by the application, then the process moves onto Block 310 where the 'tech neck' application pauses or freezes the display of the device. Alternatively, the application can reduce the brightness of the display. In cases where the 'tech neck' is not detected and the threshold time period has not passed, then the visual alert is removed from the display and the user can continue using the electronic device (Block 312).

It should be noted that an audible alert can be used in place of the visual alert and both the audible alert and the visual alert can be used simultaneously. Further, the threshold time used in Block 308 can be predeterminable and can be one or more of ten (10) seconds, twenty (20) seconds, thirty (30) seconds, sixty (60) seconds or any other value as per preferences of the user.

Figure 4:
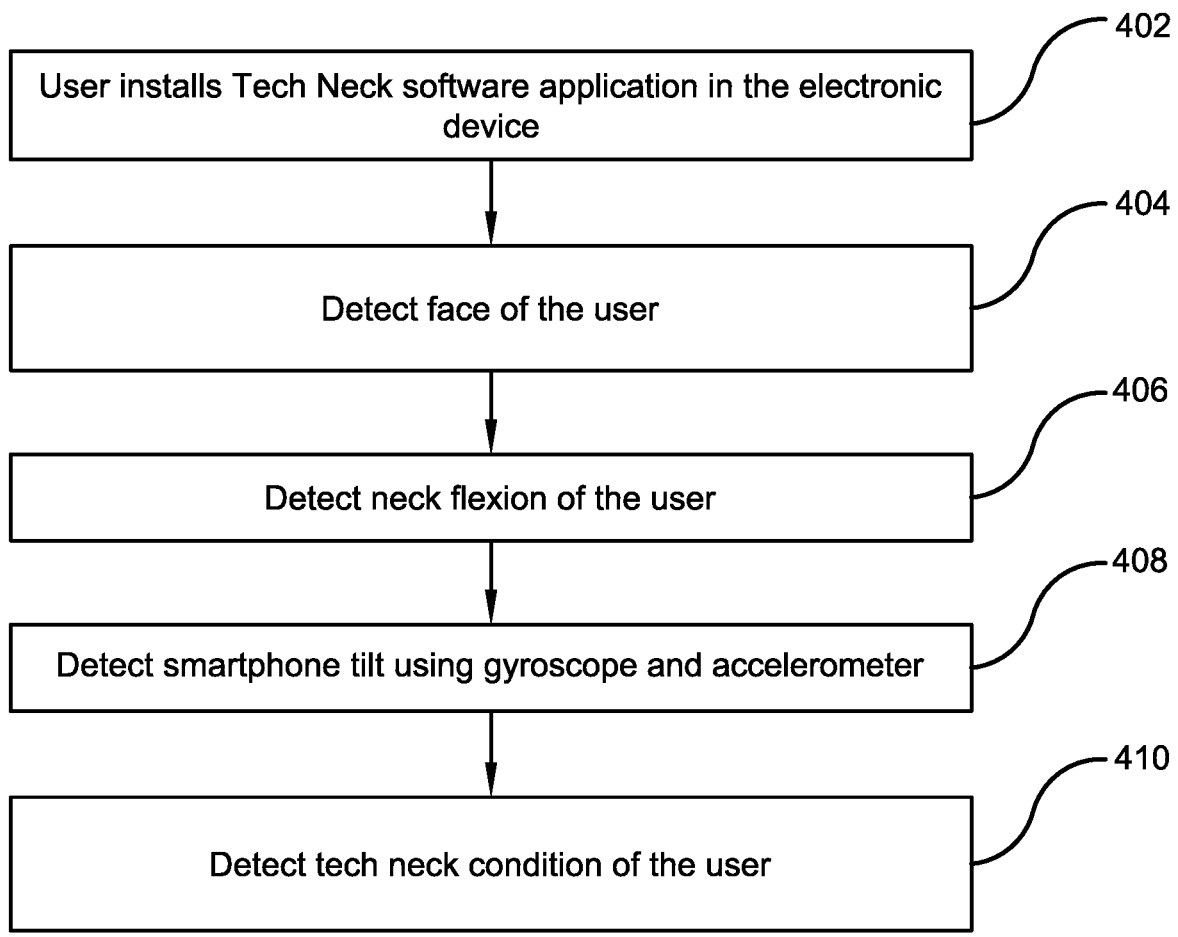
FIG. 4 illustrates a flow diagram showing the operation of the 'tech neck' software application for detecting the 'tech neck' condition of the user in accordance with the disclosed architecture.

FIG. 4 illustrates a flow diagram showing the operation of the 'tech neck' software application for detecting the 'tech neck' condition of the user in accordance with the disclosed architecture. As shown in FIG. 4, initially a user installs the computer-implemented 'tech neck' software application in an electronic device (Block 402). The 'tech neck' software application scans/detects the face of the user using the smartphone through the image capturing unit such as the camera of the electronic device (Block 404). Then, the 'tech neck' software application detects the flexion of the user using the neck position module (Block 406). Thereafter, or simultaneously, the 'tech neck' software application detects the smartphone/electronic device tilt using gyroscope and the accelerometer of the device (Block 408). Based on the detected values, the 'tech neck' condition is detected by the software application (Block 410).

Figure 5:
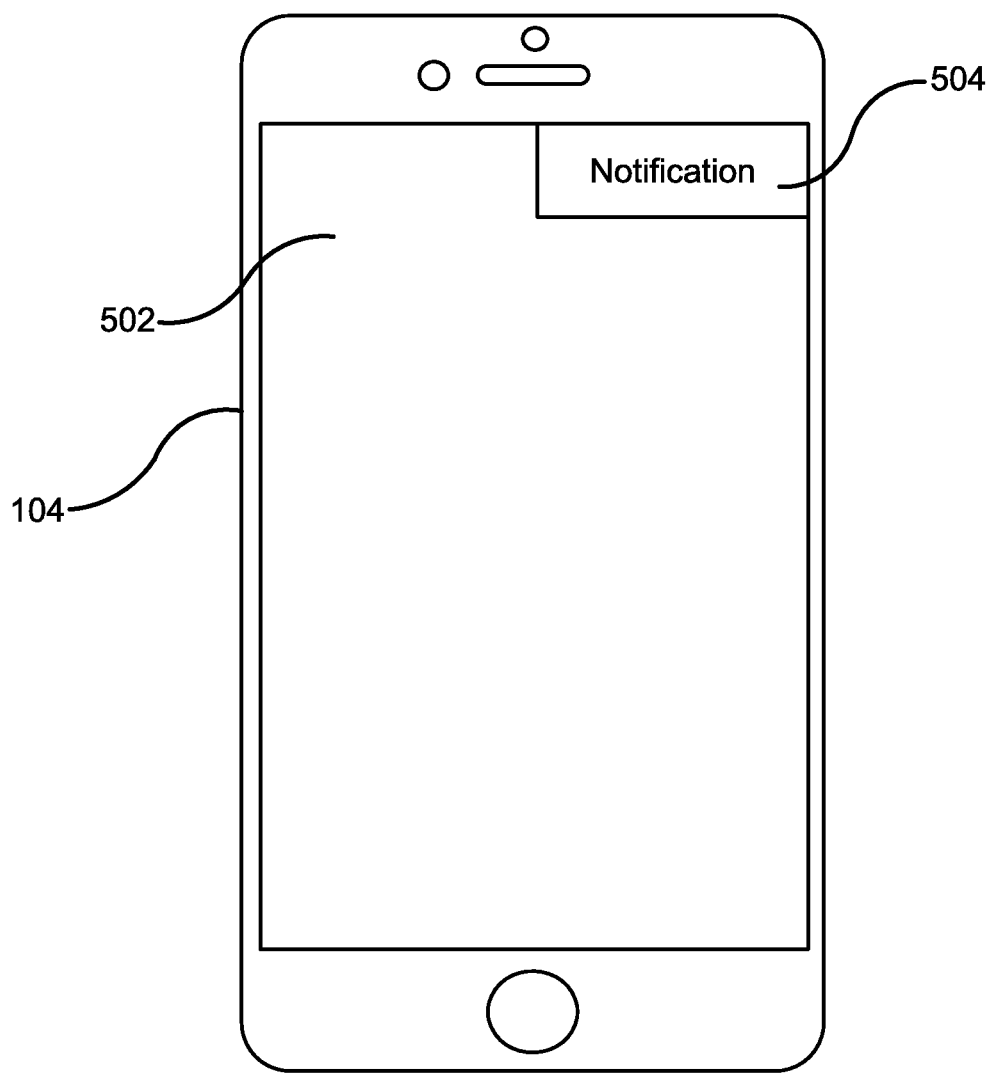
FIG. 5 illustrates a perspective view showing the visual notification displayed on the screen/display of the electronic device by the 'tech neck' software application when an unhealthy neck position of a user is detected in accordance with the disclosed architecture.

FIG. 5 illustrates a perspective view showing the visual notification displayed on screen/display of the electronic device by the 'tech neck' software application when an unhealthy neck position of a user is detected in accordance with the disclosed architecture. As stated earlier, the 'tech neck' software application 102 can work in the background when the user is using the other applications installed in the electronic device 104. Using the camera, gyroscope, and accelerometer of the electronic device 104, the application determines the flexion of the user and accordingly generates the alert notification 504 on the corner of the display 502 while the electronic device 104 is being used by a user. The notification can lead to pause of the display or minimal brightness in case the user's neck continues to be in an unhealthy position i.e., flexion of more than thirty degrees.

Figure 6:
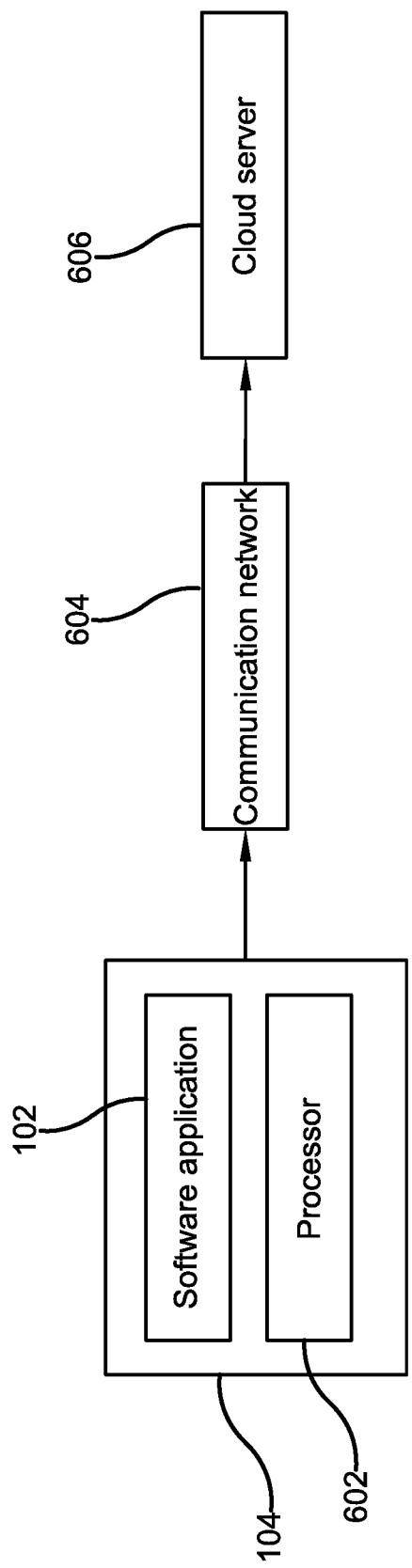
FIG. 6 illustrates a block diagram view showing the options of local processing and cloud processing for determining 'tech neck' position of a user by the computer-implemented software application of the present invention in accordance with the disclosed architecture.

FIG. 6 illustrates a block diagram view showing the options of local processing and cloud processing for determining 'tech neck' position of a user by the computer-implemented software application 102 of the present invention in accordance with the disclosed architecture. The software application 102 installed in the electronic device 104 is configured to determine 'tech neck' position of a user as discussed in various embodiments of the present invention. The software application 102 can process the position of the neck locally within the electronic device 104 using the processor 602 of the device 104. Alternatively, based on the preference of the user and processing capability of the electronic device 104, the processing to identify 'tech neck' of the user can be performed on a cloud server 606. The detected neck flexion and the smartphone tilt along with the face structure are transmitted in real-time to the cloud server 606 using the communication network 604 and result of determination of the 'tech neck' condition is transmitted to the electronic device 104 by the server 606.

The communication network 604 may be of any local area network (LAN), metropolitan area network (MAN), wide area network (WAN), a public data network (e.g., the Internet), short range wireless network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (Wi-Fi), Zigbee, Wi-Fi Direct, wireless LAN (WLAN), Bluetooth®, mobile ad-hoc network (MANET), and the like, or any combination thereof.

Figure 7:
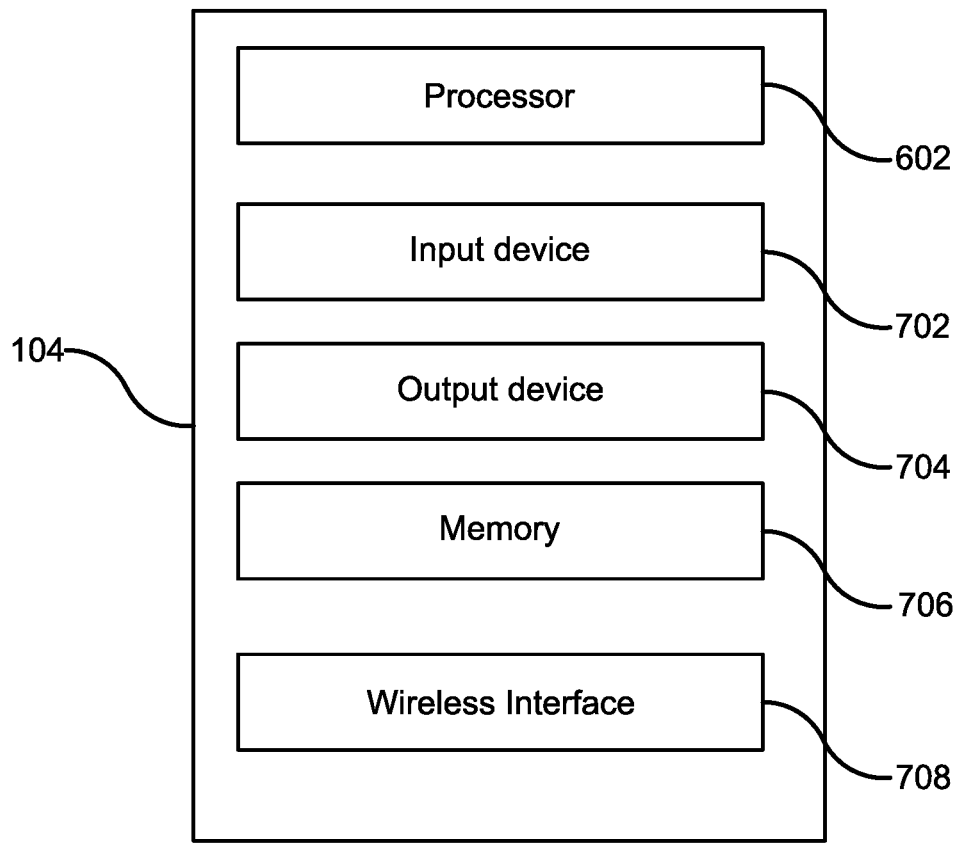
FIG. 7 illustrates an exemplary electronic device in which the computer-implemented 'tech neck' application of the present disclosure is installed in accordance with the disclosed architecture.

FIG. 7 illustrates an exemplary electronic device 104 in which the computer-implemented 'tech neck' application 102 of the present disclosure is installed in accordance with the disclosed architecture. The electronic device 104 includes several components, such as the processor 602 configured to perform one or more functions described herein in accordance with the computer implemented instructions. The electronic device 104 includes input device(s) 702 such as a mouse, keyboard, touch input device, voice input device, etc. for entering data and information. Electronic device 104 also includes one or more output device(s) 704 such as a monitor, presence-sensitive display, or other display device. Electronic device 104 has memory 706 used for storing programs (sequences of instructions) or data (e.g., program state information) on a temporary or permanent basis for use in the computer system. Memory 706 can be configured for short-term storage of information as volatile memory and therefore not retain stored contents if powered off. Examples of volatile memories include random access memories (RAM), dynamic random-access memories (DRAM), static random-access memories (SRAM), and other forms of volatile memories known in the art. The processor 602, in combination with one or more of memory 706, input device(s) 702, output device(s) 704 is utilized to detect 'tech neck' and generate alerts. The wireless connection with the cloud server 606 is provided by wireless interface 708.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "neck posture correction system", "computer-implemented 'tech neck' prevention system", "'tech neck' prevention system", and "system" are interchangeable and refer to the computer-implemented 'tech neck' prevention system 100 of the present invention. Also, as used herein "computer-implemented 'tech neck' application", "computer-implemented 'tech neck' software application", "software application" and "application" are interchangeable and refer to the computer-implemented 'tech neck' application 102 of the present invention.

Notwithstanding the forgoing, the computer-implemented 'tech neck' prevention system 100 of the present invention can be of any suitable size and configuration as is known in the art without affecting the overall concept of the invention, provided that it accomplishes the above-stated objectives. The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computer implemented 'tech neck' prevention method comprising the steps of:
   installing a software application on an electronic device for detecting a canted angle of a neck of a user of said electronic device;
   scanning a user's face and neck angle with an image scanner from said electronic device;
   recording said neck angle with said image scanner;
   detecting said canted angle of said neck of said user while the user views said electronic device; and
   alerting the user when said canted angle of said neck is greater than a predeterminable angle for a time period greater than a predeterminable time period; and
   wherein the software application comprises a face detection module configured to create a three dimensional map of the user's face and neck angle and a position of the user's eyes based on the scanning of the user's face and neck angle with the image scanner; and
   wherein the software application further comprises a neck position module in parallel with the face detection module configured to detect and calculate a position of the user's neck and calculate a neck flection area under the user's face.

2. The method of claim 1, wherein said alerting includes a visual alert on said electronic device.

3. The method of claim 1, wherein said alerting includes an audible alert on said electronic device.

4. The method of claim 1, wherein said software application operates in a background of said electronic device while the user views another application on said electronic device.

5. The method of claim 1, wherein said predeterminable angle is thirty degrees from vertical.

6. The method of claim 5, wherein said predeterminable time period is 60 seconds.

7. The method of claim 1, wherein said software application continuously scanning said user's face and said neck angle.

8. The method of claim 7, wherein said image scanner is a camera disposed on a front side of said electronic device.

9. The method of claim 8, wherein said electronic device is selected from a group consisting of a cellphone, a smartphone, a laptop, a tablet, and a smartwatch.

10. The method of claim 1, wherein said detecting of said canted angle of said neck of said user includes detecting a position of said user's face and eyes while viewing said electronic device.

11. The method of claim 10, wherein said detecting of said canted angle of said neck of said user includes detecting a neck flexion of said user.

12. The method of claim 1, wherein said alerting includes pausing a display of said electronic device.

13. The method of claim 1, wherein said alerting includes vibrating said electronic device.

14. The method of claim 11 further comprising a step of detecting a tilt of said electronic device using said electronic device's gyroscope and accelerometer.

15. The method of claim 2 further comprising a step of removing said visual alert when said canted angle of said neck is less than a predeterminable angle.

16. A computer implemented 'tech neck' prevention method comprising the steps of:
   installing a software application on an electronic device for detecting a canted angle of a neck of a user of said electronic device;
   scanning a user's face and neck angle with an image scanner from said electronic device;
   detecting said canted angle of said neck of said user while the user views said electronic device;
   alerting the user when said canted angle of said neck is greater than a predeterminable angle for a time period greater than a predeterminable time period; and
   wherein said predeterminable angle is thirty degrees from vertical; and
   wherein the software application comprises a face detection module configured to create a three dimensional map of the user's face and neck angle and a position of the user's eyes based on the scanning of the user's face and neck angle with the image scanner; and
   wherein the software application further comprises a neck position module in parallel with the face detection module configured to detect and calculate a position of the user's neck and calculate a neck flection area under the user's face; and
   wherein the software application further comprises a flexion calculation module configured to construct a virtual three dimensional triangle based on the position of the user's face and eyes to calculate a flexion or a canted angle of the user's neck.

17. The method of claim 16, wherein said alerting includes an alert selected from a group consisting of a visual alert, an audio alert, and a vibration alert on said electronic device.

18. The method of claim 17, wherein said predeterminable time period is 60 seconds.

19. A computer implemented 'tech neck' prevention method comprising the steps of:
   installing a software application on an electronic device for detecting a canted angle of a neck of a user of said electronic device;
   scanning a user's face and neck angle with an image scanner from said electronic device;
   detecting said canted angle of said neck of said user while the user views said electronic device;
   alerting the user when said canted angle of said neck is greater than a predeterminable angle for a time period greater than a predeterminable time period;
   wherein said predeterminable angle is thirty degrees from vertical;
   wherein said predeterminable time period is 60 seconds; and
   wherein said electronic device is selected from a group consisting of a cellphone, a smartphone, a laptop, a tablet, and a smartwatch; and
   wherein the software application comprises a face detection module configured to create a three dimensional map of the user's face and neck angle and a position of the user's eyes based on the scanning of the user's face and neck angle with the image scanner; and
   wherein the software application further comprises a neck position module in parallel with the face detection module configured to detect and calculate a position of the user's neck and calculate a neck flection area under the user's face; and
   wherein the software application further comprises a flexion calculation module configured to construct a virtual three dimensional triangle based on the position of the user's face and eyes to calculate a flexion or a canted angle of the user's neck; and
   wherein the software application further comprises a history module for recording a history of the user's neck flexion.

20. The method of claim 19, wherein said alerting includes an alert selected from a group consisting of a visual alert, an audio alert, and a vibration alert on said electronic device.

* * * * *